US012491089B2

(12) United States Patent
Keach

(10) Patent No.: US 12,491,089 B2
(45) Date of Patent: Dec. 9, 2025

(54) IMPLANT EXTRACTOR

(71) Applicant: Shukla Medical, St. Petersburg, FL (US)

(72) Inventor: Nicholas Christopher Keach, Lutz, FL (US)

(73) Assignee: Shukla Medical, St. Petersburg, FL (US)

( * ) Notice: Subject to any disclaimer, the term of this patent is extended or adjusted under 35 U.S.C. 154(b) by 78 days.

(21) Appl. No.: 18/576,035

(22) PCT Filed: Jul. 5, 2022

(86) PCT No.: PCT/US2022/036149
§ 371 (c)(1),
(2) Date: Jan. 2, 2024

(87) PCT Pub. No.: WO2023/278898
PCT Pub. Date: Jan. 5, 2023

(65) Prior Publication Data

US 2024/0307193 A1 Sep. 19, 2024

Related U.S. Application Data

(60) Provisional application No. 63/217,938, filed on Jul. 2, 2021.

(51) Int. Cl.
*A61F 2/46* (2006.01)

(52) U.S. Cl.
CPC .... *A61F 2/4607* (2013.01); *A61F 2002/4619* (2013.01); *A61F 2002/4627* (2013.01)

(58) Field of Classification Search
CPC . A61B 17/92; A61B 17/921; A61B 2017/922; A61B 2017/924; A61F 2002/4619
See application file for complete search history.

(56) References Cited

U.S. PATENT DOCUMENTS

| | | | | |
|---|---|---|---|---|
| 4,993,410 A | | 2/1991 | Kimsey | |
| 5,443,471 A | * | 8/1995 | Swajger ............. | A61B 17/1659 403/324 |

(Continued)

FOREIGN PATENT DOCUMENTS

| | | | |
|---|---|---|---|
| FR | 2742334 A1 | 6/1997 | |
| JP | 2017064069 A | 4/2017 | |
| WO | 2014167258 A1 | 10/2014 | |

OTHER PUBLICATIONS

IP Australia, Examination Report in counterpart application No. 2022303401, dated Aug. 28, 2024.

(Continued)

*Primary Examiner* — Anu Ramana
(74) *Attorney, Agent, or Firm* — Kim IP Law Group

(57) ABSTRACT

An implant extracting tool (100) is provided having an elongate housing (200) with a proximal end (202) configured for connection to a tool, a distal end (204) having an opening for operably engaging an implant, and an elongate recess (206) therein to the opening. A jaw (118) is slidably received within the slot and extends into the opening. A linkage assembly (280) is secured and received within the elongate recess and is pivotally secured to the jaw such that operation of the linkage slides the jaw within the slot towards and away from the opening. A lock mechanism (140) can be provided to hold the extracting tool in a locked position when clamped onto an implant.

17 Claims, 15 Drawing Sheets

(56) References Cited

U.S. PATENT DOCUMENTS

| | | | | |
|---|---|---|---|---|
| 7,682,363 | B2 * | 3/2010 | Burgi | A61F 2/4609<br>606/88 |
| 10,398,569 | B2 * | 9/2019 | Jaumard | A61F 2/4601 |
| 10,398,596 | B2 | 9/2019 | Hunter | |
| 11,399,961 | B2 * | 8/2022 | Gosik-Wolfe | A61F 2/4603 |
| 11,779,468 | B2 * | 10/2023 | Keach | A61B 17/921<br>606/99 |
| 12,109,129 | B2 * | 10/2024 | Sweitzer | A61F 2/4603 |
| 12,109,130 | B2 * | 10/2024 | Sweitzer | A61F 2/4612 |
| 2003/0220698 | A1 | 11/2003 | Mears et al. | |
| 2006/0200162 | A1 | 9/2006 | Farling et al. | |
| 2008/0262503 | A1 | 10/2008 | Muller | |
| 2016/0059403 | A1 * | 3/2016 | Mugnier | A61B 17/14<br>16/422 |
| 2016/0067057 | A1 | 3/2016 | Jones et al. | |
| 2019/0374349 | A1 * | 12/2019 | Müller | A61F 2/4607 |
| 2020/0121474 | A1 | 4/2020 | Pendleton et al. | |
| 2023/0220698 | A1 | 7/2023 | Johnston et al. | |

OTHER PUBLICATIONS

Japan Patent Office, Office Action in counterpart application No. 2023-581071 dated Oct. 15, 2024.

International Search Report in International Application No. PCT/US2022/036149 dated Sep. 29, 2022.

Written Opinion of the International Searching Authority in International Application No. PCT/US2022/036149 dated Sep. 29, 2022.

Japan Patent Office, Office Action issued in counterpart application No. 2023-581071, dated Apr. 8, 2025.

European Patent Office, Office Action issued in counterpart application No. 22 747 895.5, dated May 27, 2025.

* cited by examiner

IMPLANT EXTRACTOR

CROSS-REFERENCE TO RELATED APPLICATION(S)

This is a national stage application filed under 35 U.S.C. § 371 of International Patent Application No. PCT/US2022/036149, filed Jul. 5, 2022, which claims the benefit of U.S. Provisional Patent Application No. 63/217,938, filed Jul. 2, 2021, the disclosures of which are incorporated herein by reference in their entireties.

This invention relates to a surgical device for use in implant extraction such as the extraction of implanted hip stem implants and prostheses.

BACKGROUND

Surgeons use implant extracting devices as tools to assist with the removal of implanted surgical implants such as hip stems and prostheses. These devices allow a surgeon to use the tool to clamp onto a portion of the implant, such as a trunnion or the like, and then apply forces to the tool to extract the implant.

BRIEF SUMMARY

Despite the existence of conventional implant extracting devices, there remains a need for an implant extracting device that allows for easy removal and replacement of the implant engaging components that can wear after repeated use. Moreover, there remains a need for an implant extracting device that provides a movable implant engaging jaw that remains in a desired commanded position even when no external forces beside gravity is acting on the jaw. In addition, there remains a need for a shorter implant extracting device than those currently offered without compromising the function of the tool. These and other benefits of the invention are described in greater detail herein.

In one exemplary embodiment, an implant extracting tool is disclosed that has an elongate housing with a proximal end configured for connection to an extraction tool, a distal end having an opening for operably engaging the implant, and an elongate recess therein with a slot extending from the elongate recess to the opening. A jaw is slidably received within the slot and operably extending into the opening. A linkage is secured and received within the elongate recess of the housing. The linkage is pivotally secured to the jaw such that operation of the linkage slides the jaw within the slot towards and away from the opening.

Other disclosed embodiments can include an insert with teeth for engaging the implant operably secured to the extracting tool. The insert and jaw can be detachably secured to the implant extracting tool and easily removed and replaced as needed. The jaw is detachably secured within the elongate housing. Also, a lock mechanism can be provided to hold the extracting tool in a locked position when clamped onto an implant.

An implant extractor comprising: an elongate housing having: a proximal end configured for connection to an extraction tool, a distal end for operably engaging an implant, and an elongate recess extending therein; a jaw slidably received within the elongate recess and extending to the distal end of the elongate housing; a linkage assembly within the elongate recess of the housing, the linkage assembly including a linkage pivotally secured to the jaw such that operation of the linkage assembly slides the jaw towards and away from the distal end.

The elongate housing includes an opening at the distal end configured for receiving an implant. The elongate recess is in fluid communication with the opening.

The linkage assembly includes: a rod assembly; a proximal link operatively connected to the rod assembly; a proximal end of the rod assembly pivotably connected to a distal end of the proximal link; an intermediate link operatively connected to the rod assembly; and a bell link operatively connected to the intermediate link and the jaw, wherein placement of the handle in a first position causes the jaw to disengage a trunnion of a hip stem implant, and placement of the handle in a second position causes the jaw to engage the trunnion of the hip stem implant.

The implant extractor further comprising a handle pivotably connected to the housing and operatively engaged with the proximal link. The implant extractor further comprising a handle pivotably connected to the housing and operatively engaged with the linkage assembly. The placement of the handle in a first position causes the jaw to move to a disengagement state, and placement of the handle in a second position causes the jaw to move to an engagement state.

The rod assembly is a telescopic rod assembly. The rod assembly comprises: a proximal link connector operatively connected to the proximal link; an intermediate link connector operatively connected to the intermediate link; and a rotatable shaft rotatable about the proximal link connector and operatively engage with the intermediate link connector.

The implant extractor further comprising a dial operatively connected to the central rotatable shaft, whereby rotation of the dial in a first direction operates to unthread the intermediate link connector from the central rotatable shaft, and whereby rotation of the dial in a second direction opposite the first direction operates to thread the intermediate link connector into the central rotatable shaft.

The implant extractor further comprising a jaw link coupling the bell link to the jaw. The implant extractor further comprising a locking key operatively connected to the proximal link and moveable between an unlocked position and a locked position. The locking key locks the position of the handle in a fixed position. The locking key locks the position of the proximal link in a fixed position.

The jaw is detachably secured within the elongate housing. The implant extractor further including a removable insert detachably secured to the housing at a distal end, the removable insert having a surface for engaging an implant and an opening for receiving the jaw therethrough.

The implant extractor further comprising a cam lock configured to lock the linkage assembly in a fixed position. The implant extractor further comprising a cam lock configured to apply a locking force and lock the linkage assembly in a fixed position.

Other features and advantages of the subject disclosure will be apparent from the following more detailed description of the exemplary embodiments, taken in conjunction with the accompanying drawings which illustrate, by way of example, the principles of the subject disclosure.

BRIEF DESCRIPTION OF THE SEVERAL VIEWS OF THE DRAWINGS

The foregoing summary, as well as the following detailed description of the exemplary embodiments of the subject disclosure, will be better understood when read in conjunction with the appended drawings. For the purpose of illustrating the subject disclosure, there are shown in the drawings exemplary embodiments. It should be understood, however, that the invention is not limited to the precise arrangements and instrumentalities shown.

In the Drawings.

DETAILED DESCRIPTION

Figure 1:
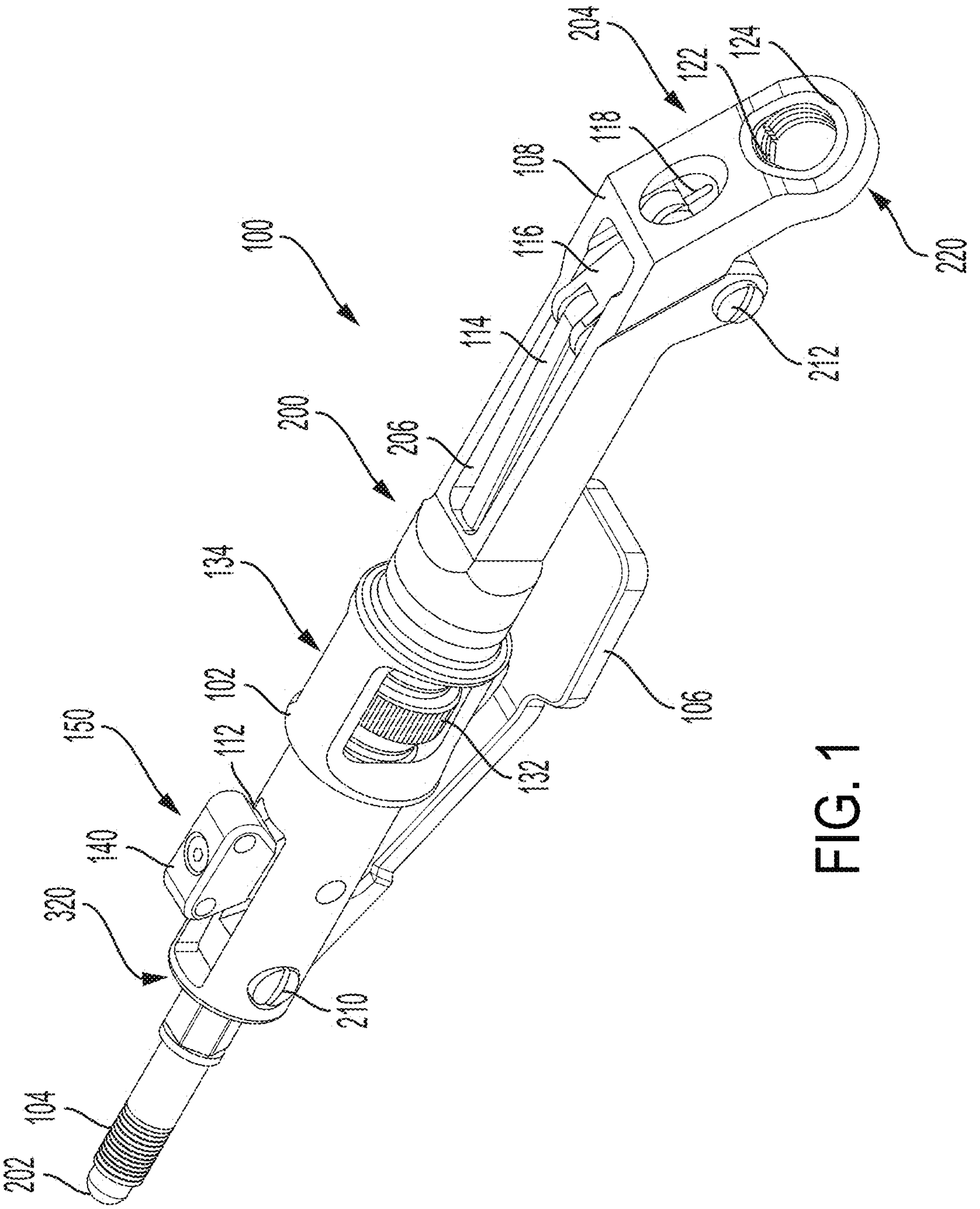
FIG. 1 is a distal perspective view of a hip stem implant extractor in accordance with an exemplary embodiment of the subject disclosure.
Figure 2:
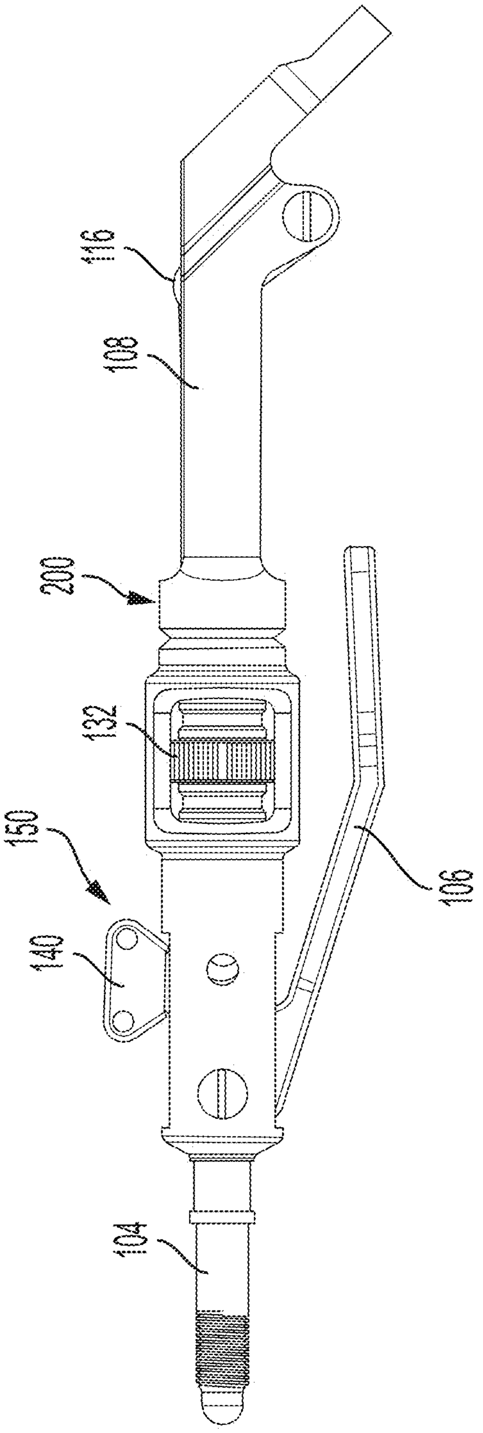
FIG. 2 is a left side view of the hip stem implant extractor of FIG. 1.
Figure 3:
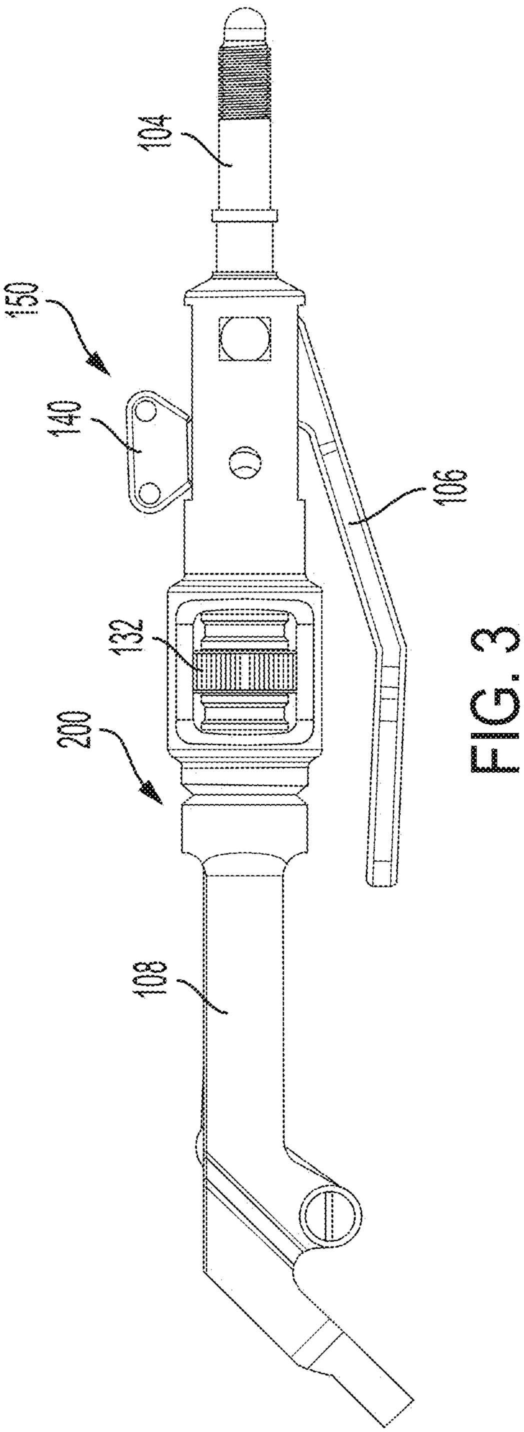
FIG. 3 is a right side view of the hip stem implant extractor of FIG. 1.
Figure 4:
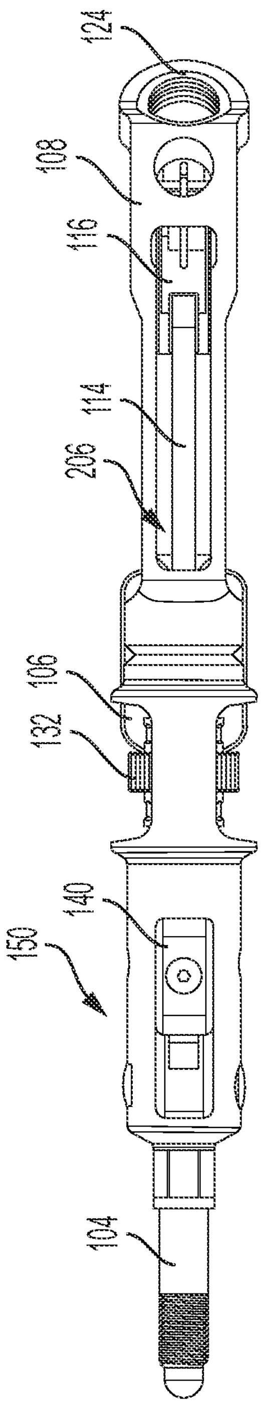
FIG. 4 is a posterior view of the hip stem implant extractor of FIG. 1.
Figure 5:
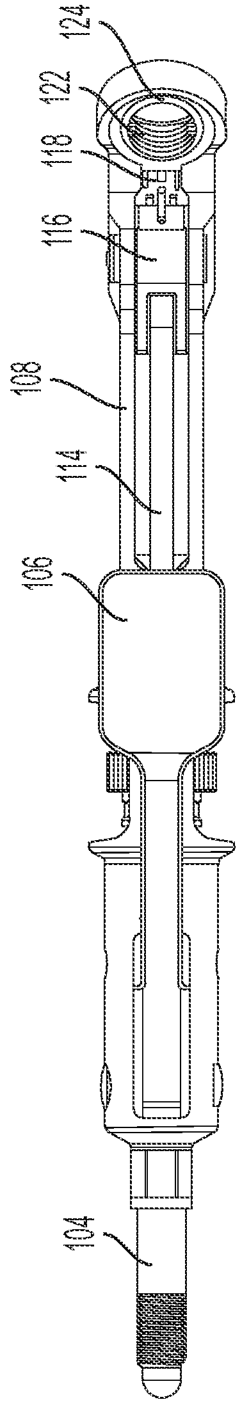
FIG. 5 is an anterior view of the hip stem implant extractor of FIG. 1.
Figure 7:
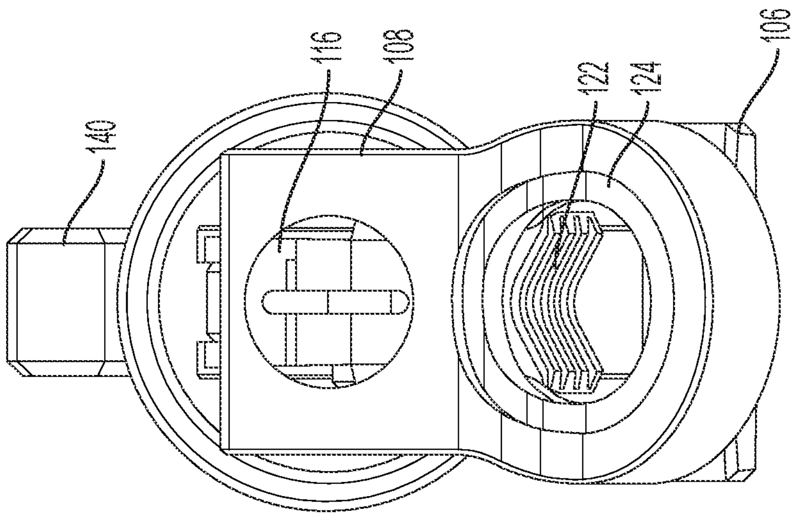
FIG. 7 is a bottom view of the hip stem implant extractor of FIG. 1.
Figure 6:
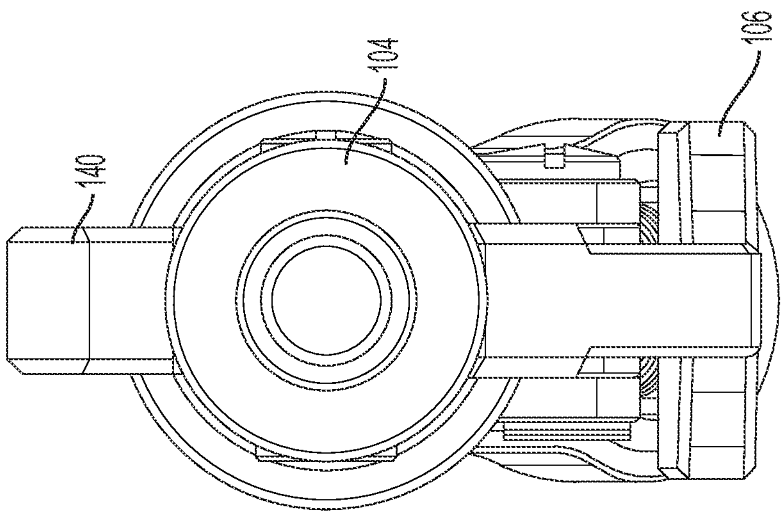
FIG. 6 is a top view of the hip stem implant extractor of FIG. 1.

Reference will now be made in detail to the various embodiments of the subject disclosure illustrated in the accompanying drawings. Wherever possible, the same or like reference numbers will be used throughout the drawings to refer to the same or like features. It should be noted that the drawings are in simplified form and are not drawn to precise scale. Certain terminology is used in the following description for convenience only and is not limiting. Directional terms such as top, bottom, left, right, above, below and diagonal, are used with respect to the accompanying drawings. The term "distal" shall mean away from the center of a body. The term "proximal" shall mean closer towards the center of a body and/or away from the "distal" end. The words "inwardly" and "outwardly" refer to directions toward and away from, respectively, the geometric center of the identified element and designated parts thereof. Such directional terms used in conjunction with the following description of the drawings should not be construed to limit the scope of the subject disclosure in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art. "Exemplary" as used herein shall mean serving as an example.

Throughout this disclosure, various aspects of the subject disclosure can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more embodiments. One skilled in the relevant art will recognize, in light of the description herein, that the present disclosure can be practiced without one or more of the specific features or advantages of a particular exemplary embodiment. In other instances, additional features and advantages may be recognized in certain embodiments that may not be present in all exemplary embodiments of the subject disclosure.

The subject disclosure provides an implant extractor medical device for use in orthopedic surgeries. In accordance with an exemplary embodiment, the implant extractor is a hip stem implant extractor 100. FIGS. 1-28 show the construction of the exemplary hip stem implant extractor 100 constructed in accordance with the subject disclosure.

The hip stem implant extractor 100 includes a linkage assembly 280 (FIG. 12) operably secured within an elongate housing 200. The linkage assembly 280 is coupled to a jaw 118 which is movable between first and second positions under the influence of a cam lock 320 having pivotable handle 106. As further discussed below, the jaw is configured for clamping e.g., a trunnion (not shown).

The elongate housing 200 has a proximal end 202 and opposite distal end 204. The elongate housing includes a proximal body member 102 joined to a distal body member 108. A continuous recess or elongate continuous recess 206 extends through the proximal body member and the distal body member to operably receive the linkage assembly 280 therein.

The proximal body member 102 includes a tool connector 104 adapted for connection to an extraction tool, e.g., a T-handle or C-frame, and the like. In the present exemplary embodiment, the tool connector is a threaded tool connector.

The distal body member 108 is configured as best shown in FIG. 1 and includes a main body portion and a bent arm portion that extends from the main body portion about 40-50 degrees, including 35, 45, and 55 degrees, from a longitudinal axis of the main body portion. The bent arm portion includes a through hole or opening 220 for receiving an implant therein e.g., a trunnion of a hip stem implant. The continuous recess 206 extends to the opening 220. The opening can include an insert 124 detachably secured thereto. The insert 124 can include grip enhancing features e.g., teeth 122, ridges or the like, about its inner facing surfaces. The insert 124 also includes an opening 125 (FIG. 8) in a circumferential wall thereof to receive the distal end of the jaw 118. When the insert is assembled to the opening 220, the opening 125 is aligned with the continuous recess 206 and in fluid communication therewith. The insert 124 is a removable insert detachably secured to the housing 200 at the distal end 204, the removable insert 124 has a surface for engaging the implant and an opening 125 for receiving the jaw 118 therethrough.

Figure 10:
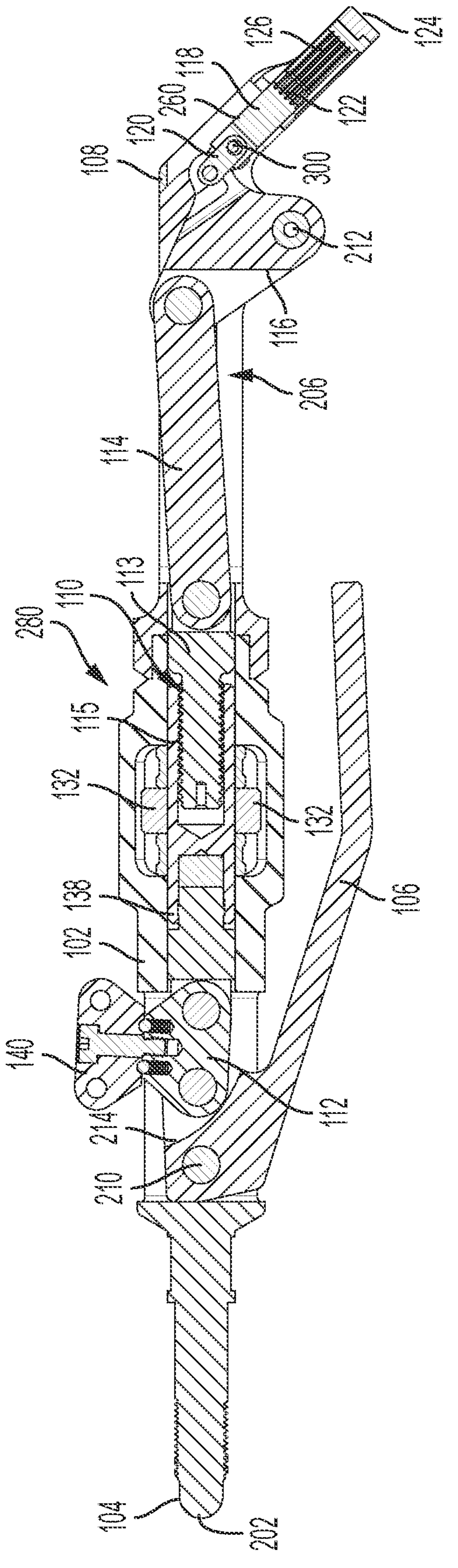
FIG. 10 is a longitudinal cross-sectional view of the hip stem implant extractor of FIG. 1.
Figure 12:
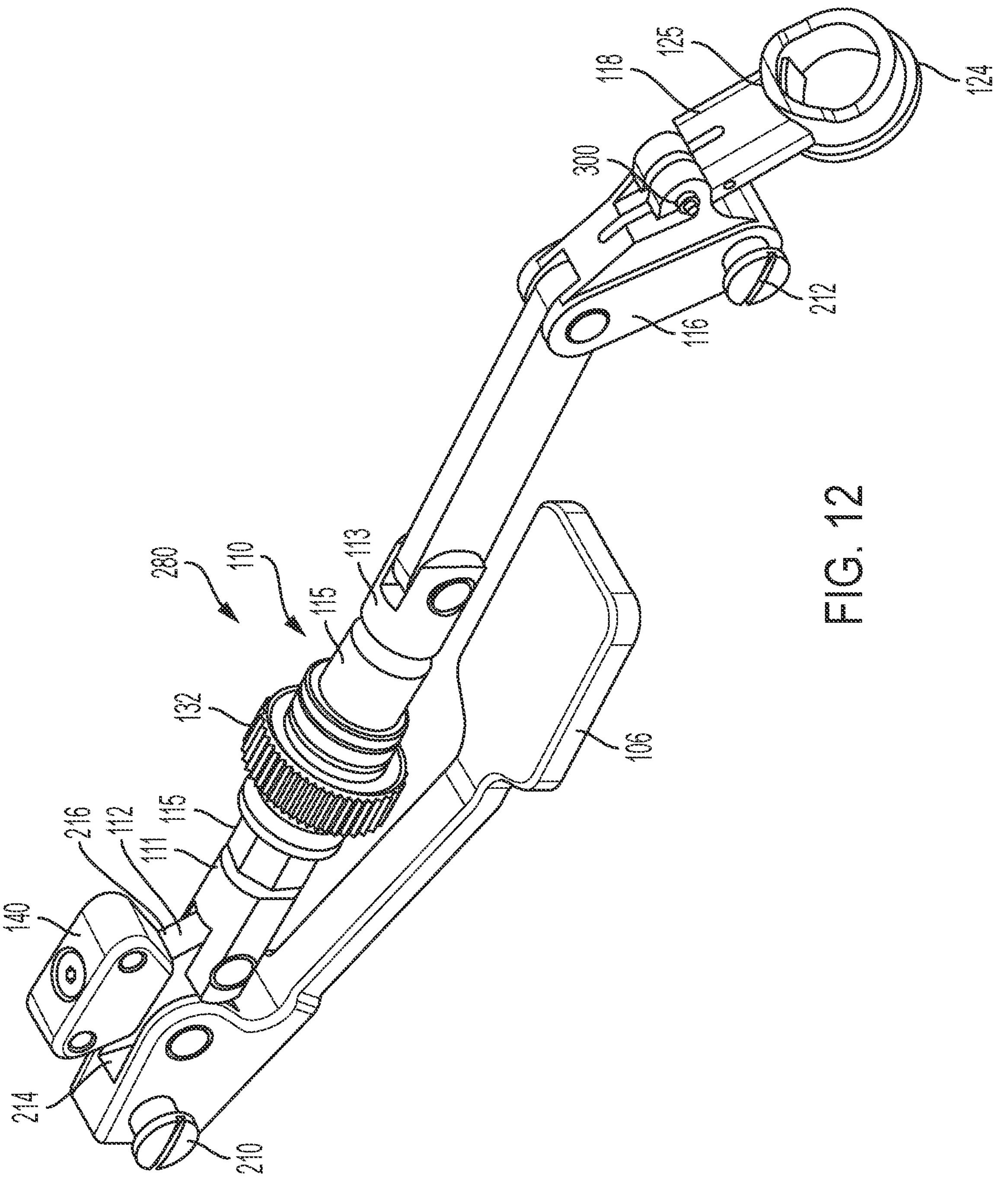
FIG. 12 is a distal perspective view of a linkage assembly of the hip stem implant extractor of FIG. 1 in accordance with an exemplary embodiment of the subject disclosure.
Figure 13:
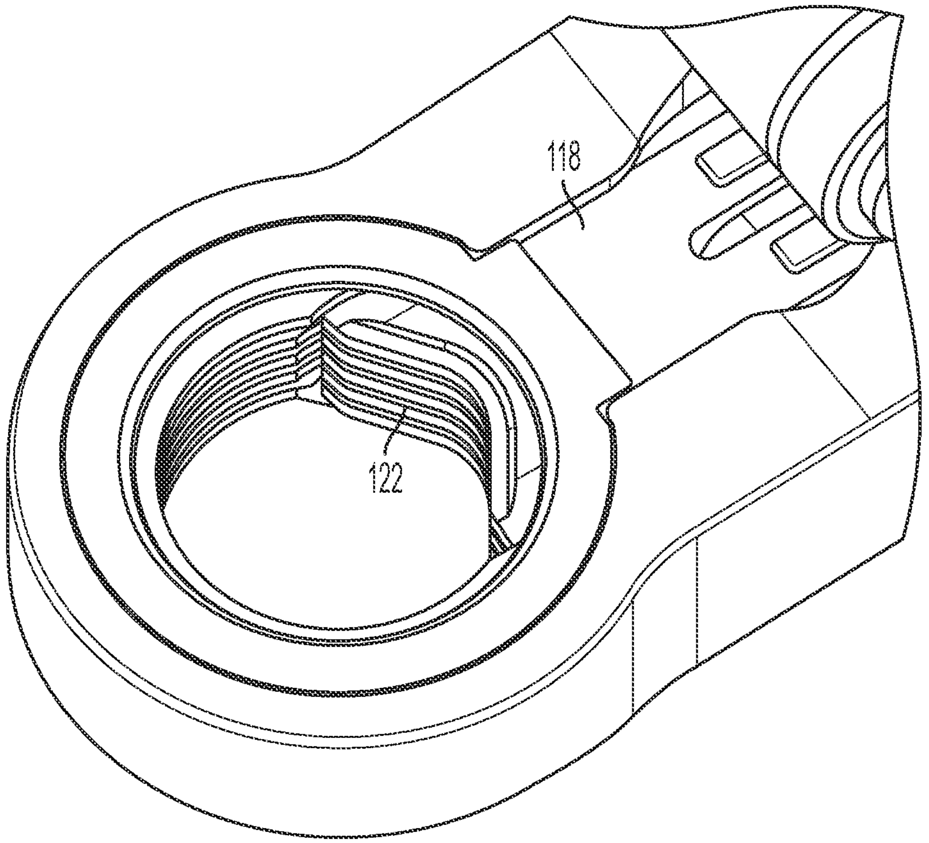
FIG. 13 is an enlarged, partial, perspective view of a distal end of the hip stem implant extractor of FIG. 1.
Figure 14:
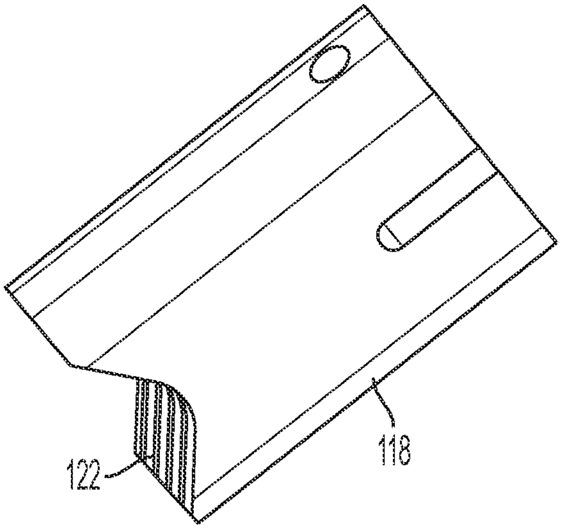
FIG. 14 is an enlarged perspective view of a jaw of the hip stem implant extractor of FIG. 1.

As best shown in FIGS. 10 & 12, the linkage assembly 280 includes a proximal link 112 having a cam race 216. The proximal link 112 is pivotally secured to the cam lock 320 having an elongate handle 106 and a cam 214 that operably engages the cam race 216. The elongate handle 106 is operatively connected to the proximal link 112 about its proximal end, as best shown in FIG. 10. The opposite distal end of the proximal link 112 is pivotally secured to a proximal link connector 111. The opposite end of the proximal link connector operably engages a rotating shaft 115 that threadably engages an intermediate link connector 113.

The handle 106 is pivotably connected to the housing 200 and operatively engaged with the linkage assembly 280. The handle 106 is pivotably connected to the housing and operatively engaged with the rod assembly 110. Placement of the handle 106 in a first position causes the jaw 118 to move to a disengagement state, and placement of the handle 106 in a second position causes the jaw 118 to move to an engagement state The cam lock 320 is configured to lock the linkage assembly in a fixed position. The cam lock 320 is configured to apply a locking force and lock the linkage assembly 280 in a fixed position.

Figure 15:
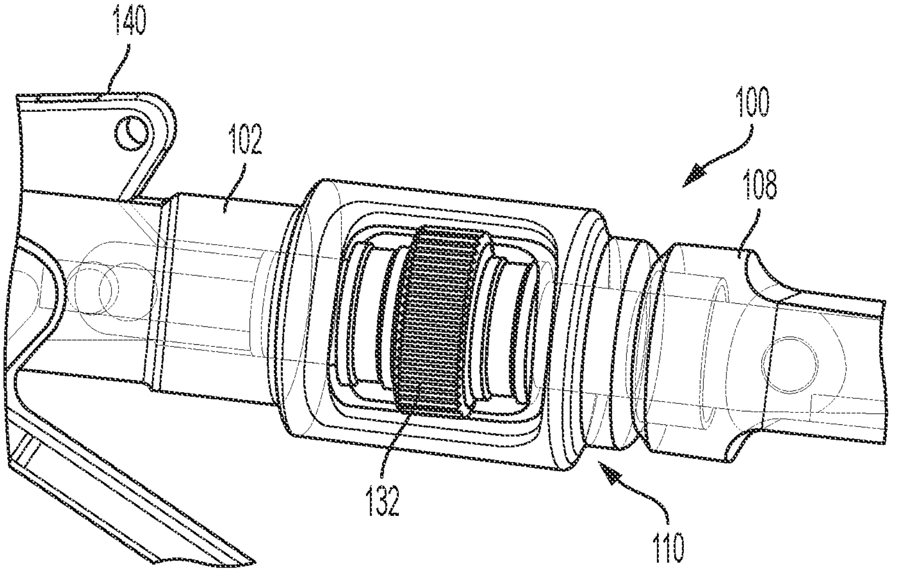
FIG. 15 is a partial enlarged isometric view of a central portion of the hip stem implant extractor of FIG. 1 with the external housing shown as transparent for purposes of illustrating the internal components of the implant extractor.
Figure 16:
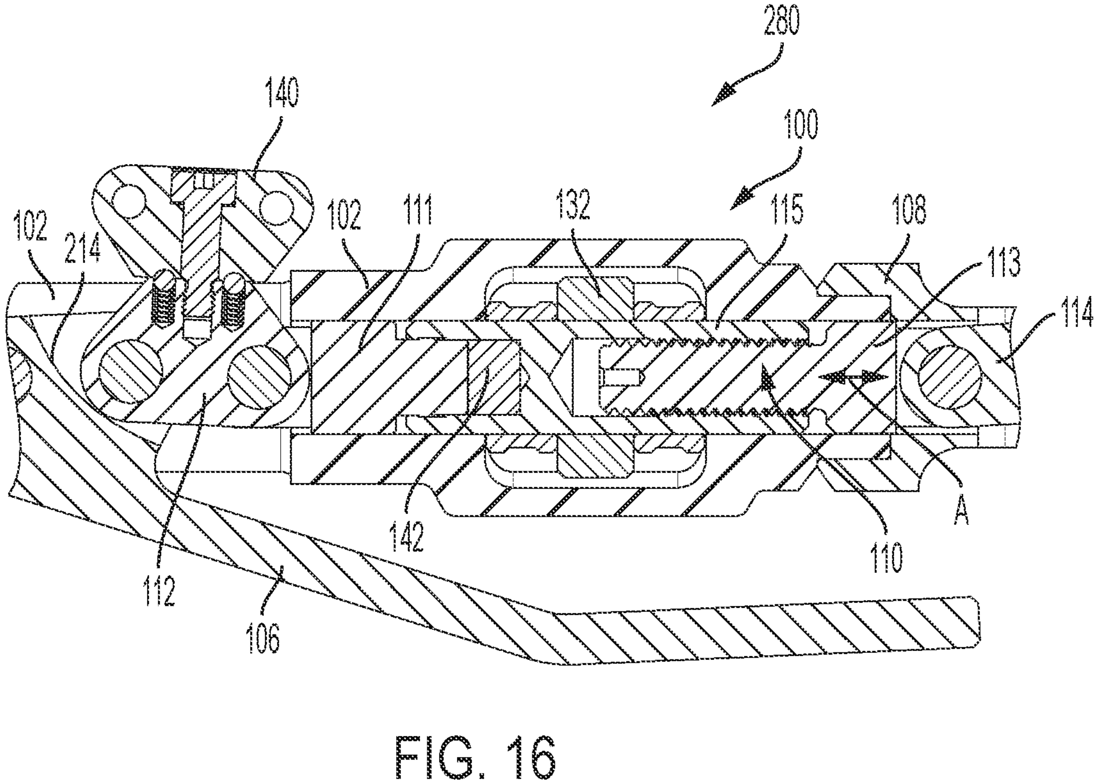
FIG. 16 is a left, cross-sectional view of a central portion of the hip stem implant extractor of FIG. 1.
Figure 17:
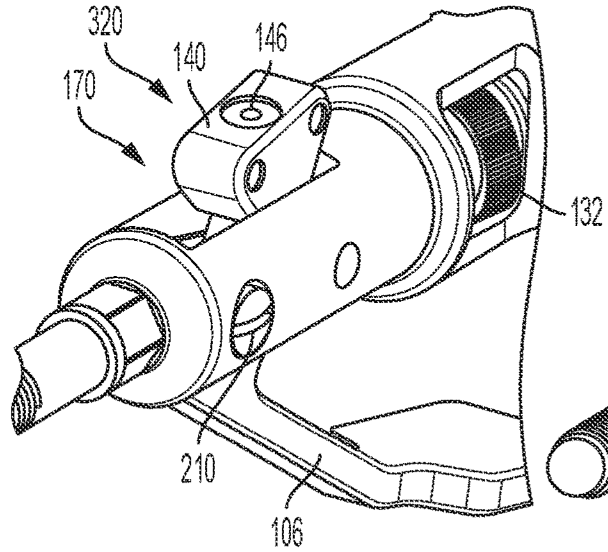
FIG. 17 is a partial, left, perspective view of the hip stem implant extractor of FIG. 1, with the handle in an unlocked position.

As best shown in FIGS. 15 & 16, the linkage assembly 280 includes a rod assembly 110 that is situated in part in the proximal body member 102 and in part in the distal body member 108. The rod assembly is configured as a telescopic rod assembly. A proximal end of the telescopic rod assembly 110 includes the proximal link connector 111 that is pivotably connected to a distal end of the proximal link 112. A distal end of the telescopic rod assembly 110 includes the intermediate link connector 113 that is pivotably connected to a proximal end of an intermediate link 114. The intermediate link connector 113 includes a treaded shaft extending proximally for threadedly engaging the telescopic rod assembly 110. The telescopic rod assembly 110 comprises the central rotatable shaft 115 which is configured to rotate about the proximal link connector 111 and threadedly engage the intermediate link connector 113.

In sum, the linkage assembly 280 includes a rod assembly 110, a proximal link 112 operatively connected to the rod assembly 110, a proximal end of the rod assembly 110 pivotably connected to a distal end of the proximal link 112, an intermediate link 114 operatively connected to the rod assembly 110, and a bell link 116 operatively connected to the intermediate link 114 and the jaw 118. The rod assembly 110 comprises a proximal link connector 111 operatively connected to the proximal link 112, an intermediate link connector 113 operatively connected to the intermediate link 114, and a rotatable shaft 115 rotatable about the proximal link connector 111 and operatively engaged with the intermediate link connector 113.

Figure 8:
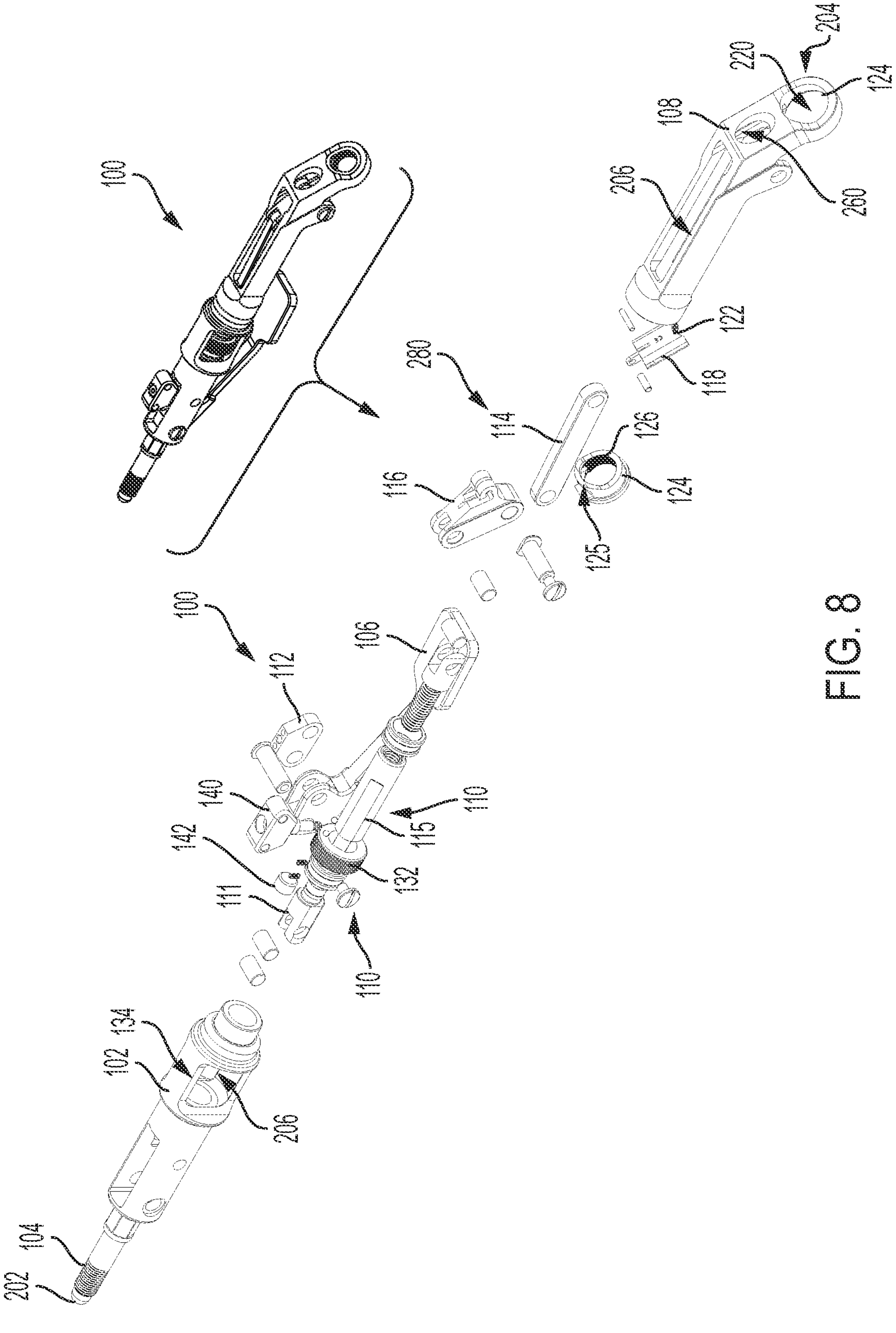
FIG. 8 is an exploded perspective view of the hip stem implant extractor of FIG. 1.
Figure 9:
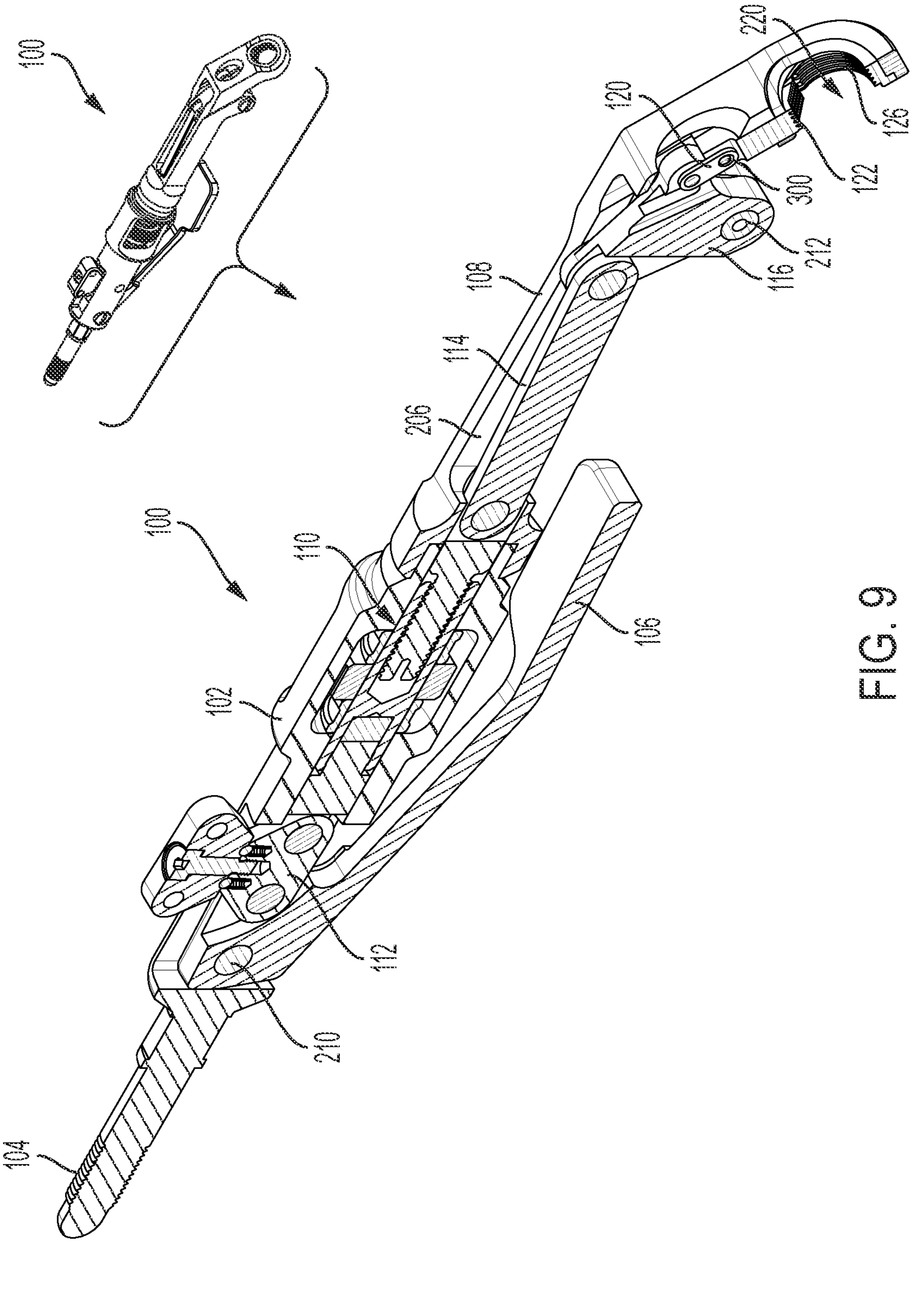
FIG. 9 is a perspective longitudinal cross-sectional view of the hip stem implant extractor of FIG. 1.

A manually actuatable dial 132 operably engages the rotating shaft 115 to adjust the position of the intermediate link connector 113 to be infinitely positionable along the path defined by arrows A (FIG. 16) of its threaded engagement. As shown in FIG. 8, the rotating shaft 115 includes a plurality of lateral flats for operatively engaging corresponding lateral flats about inner surfaces of the dial 132. For example, the plurality of flats about the rotating shaft can be hexagonal in shape, while the corresponding lateral flats of the dial are correspondingly hexagonal in shape.

Figure 11:
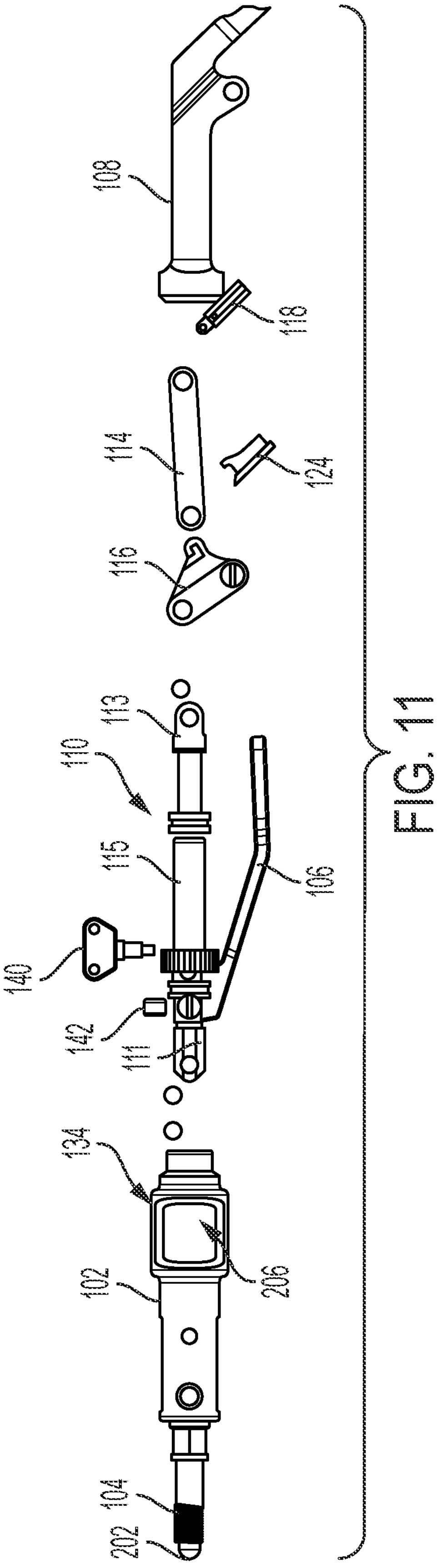
FIG. 11 is an exploded view of the hip stem implant extractor of FIG. 1.

The opposite end of the link connector 113 is pivotally secured to one end of the elongate intermediate link 114. The opposite end or distal end of the intermediate link 114 is pivotally secured to a bell link 116. The jaw 118 is pivotally secured to an opposite side or distal end of the bell link 116 with jaw link 120 at pivot 300 (FIGS. 9, 10 and 12) and operably extends through insert 124. The bell link 116 can be configured e.g., as shown in FIG. 11, having a substantially triangular shape with three pivot points, a proximal pivot, a distal pivot, and a lateral pivot. The proximal pivot is pivotably engaged with the intermediate link and the distal pivot is pivotably engaged with the jaw, while the lateral pivot is pivotably engaged with the distal body member. Both the jaw 118 (similar to the insert 124) can include grip enhancing features, such as, teeth 126, ridges or the like for operably engaging an implant, e.g., a trunnion of a hip stem implant.

As best shown in FIGS. 1 & 10, the linkage assembly 280 of FIG. 12 is operably secured within the continuous recess 206 of the housing 200 with the handle pivotally secured to the proximal body member 102 at pivot 210 and the bell link 116 pivotally secured to the distal body member 108 at pivot 212. The jaw 118 extends within and is slidable within the continuous recess 206 towards the proximal end 204. Openings within the proximal body member 102 provide access to the dial 132 whereby the position of the jaw 118 within the opening 220 can be selected by a user rotating the dial 132 about the rotating shaft one way or the other to allow for fine adjust of the amount of force applied to the jaw via the cam lock. That is, rotating the dial 132 urges the intermediate link connector 113 in one or the other direction along the continuous recess 206, in other words proximally or distally along the housing, thereby moving the intermediate link 114 to pivot the bell link 116 about pivot 212, and thereby cause the jaw 118 to move along the slot 260 (FIG. 8) in the distal body member in which the jaw 118 sits.

In sum, the dial 132 is operatively connected to the central rotatable shaft 115, whereby rotation of the dial 132 in a first direction operates to unthread the intermediate link connector 113 from the central rotatable shaft 115, and whereby rotation of the dial 132 in a second direction opposite the first direction operates to thread the intermediate link connector 113 into the central rotatable shaft.

Figure 18:
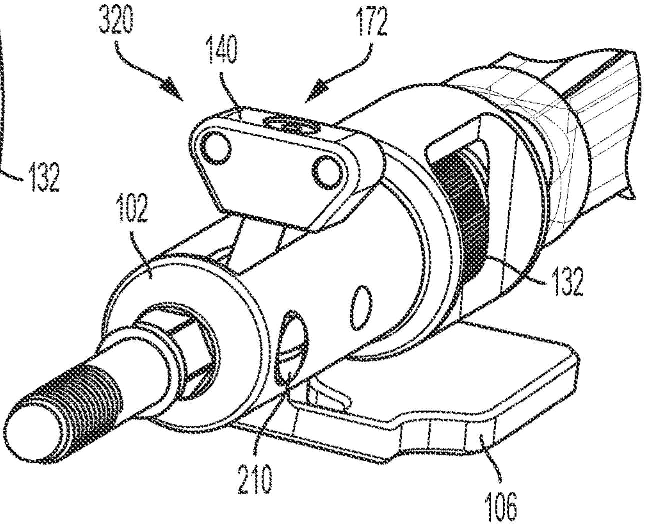
FIG. 18 is a partial, left, perspective view of the hip stem implant extractor of FIG. 1 with the handle in a locked position.
Figure 19:
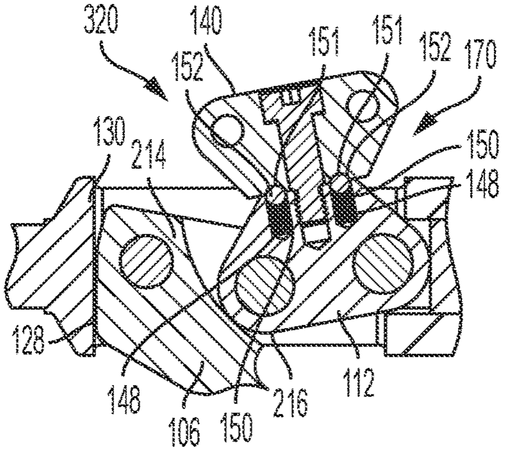
FIG. 19 is an enlarged, cross-sectional view of a central portion of the hip stem implant extractor of FIG. 17 in the unlocked position.
Figure 20:
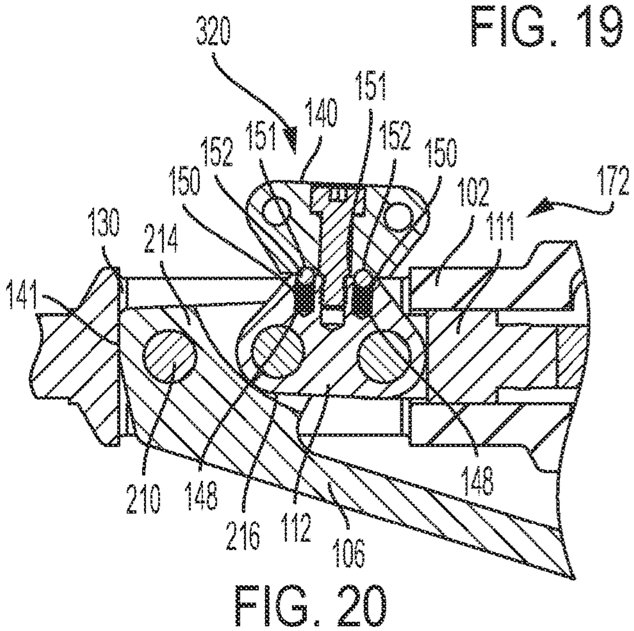
FIG. 20 is an enlarged, cross-section al view of the central portion of the hip stem implant extractor of FIG. 18 in the locked position.

Additional clamping force (in addition to the force applied via the dial) can then be applied to the jaw 118 and thereon to an implant (e.g., a trunnion) in the opening by moving the handle from its open position 170 (FIGS. 17 & 19) to its closed position 172 (FIGS. 18 & 20). This causes the handle 106 to pivot about pivot 210 thereby urging cam 214 to operably engage cam race 216 of the proximal link 112 thereby urging the rotating shaft 115 toward the distal end 204 and causing the linkage assembly 280 to move the jaw 118 toward the opening 220.

More specifically, when the handle 106 is in the unlocked or fully opened position 170 (FIGS. 17 & 19), a first surface 128 at the proximal end of the handle 106 abuts a distally facing surface 130 of the proximal body member 102 and the cam 214 at the proximal end of the handle abuts a distally facing cam race 216 of the proximal link 112. With the handle unlocked, the user can adjust the length of the linkage assembly 280 to an appropriate length for receiving a subject implant in the opening to be gripped and to increase or decrease the preload or initial position (i.e., command position) of the jaw 118 within the housing or on an implant to be gripped. To do so, the user rotates the dial 132 having opening 134 corresponding to the circumferential shape of the central rotatable shaft 115, whereby the central rotatable shaft rotates in the same direction of rotation as the dial. Rotation of the central rotatable shaft in a first direction operates to unthread the intermediate link connector 113 from a distal internally threaded end of the central rotatable shaft. Simultaneously, a proximal cylindrical socket end of the central rotatable shaft rotates freely about a distal end of the proximal link connector 111. Likewise, rotation of the central rotatable shaft in the second direction operates to thread the intermediate link connector 1133 to threads of the central rotatable shaft 115.

Rotation of the central rotatable shaft in the first direction moves the intermediate link 114, the bell link 116, the jaw link 120 and the jaw 118 in a distal direction to increase the preload on a subject implant in the opening 220 or adjust the position of the jaw within the continuous recess 206 of the housing. Conversely, rotation of the central rotatable shaft in a second direction opposite the first direction operates to thread the intermediate link connector 113 into the distal internally threaded end of the central rotatable shaft. Simultaneously, the proximal cylindrical socket end of the central rotatable shaft rotates freely about a distal end of the proximal link connector 111. The jaw link 120 links or couples the jaw to the bell link. In other words, rotation of the central rotatable shaft in the second direction moves the intermediate link 114, the bell link 116, the jaw link 120 and the jaw 118 in a proximal direction to decrease the preload on a subject implant within the opening 220 or adjust the position of the jaw within the continuous recess 206.

Once the linkage assembly 280 is properly adjusted to the receive the subject implant to be extracted and the preload to be applied thereto, the handle 106 is moved from the unlocked position 170 (FIGS. 17 & 19) to the locked position 172 (FIGS. 18 & 20), whereby the handle 106 moves the proximal link 112 in the direction of the telescopic rod assembly 110, thereby moving the telescopic rod assembly, the intermediate link 114, the bell link 116, the jaw link 120 and the jaw in a distal direction to urge the aforementioned engaging ridges, teeth, or the like 122, 126 to grip the subject implant within the opening 220.

At the same time and as best shown in FIG. 20, a second surface 141 at a proximal end of the handle 106 comes into abutment with a distally facing surface 130 of the proximal body member 102. This creates a slight over-bend of the proximal link 112 (FIG. 20) thereby locking the handle in a locked position which keeps the downstream links in a locked position and the jaw 118 in a clamped position about the trunnion. Preferably, the proximal cylindrical socket end of the central rotatable shaft 115 contains a compressible bushing 142 (FIG. 16). The compressible bushing 142 can be fabricated from a resilient polymer, such as, polyetherimide, or other generally stiff yet resilient polymers suitable for the intended purposes as a rigid compression member.

Figure 21:
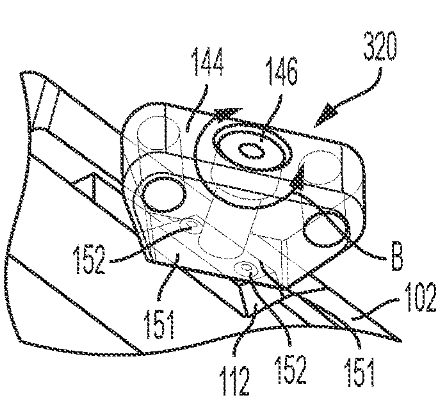
FIG. 21 is a perspective view of a rotatable locking key of the hip stem implant extractor of FIG. 1.
Figure 22:
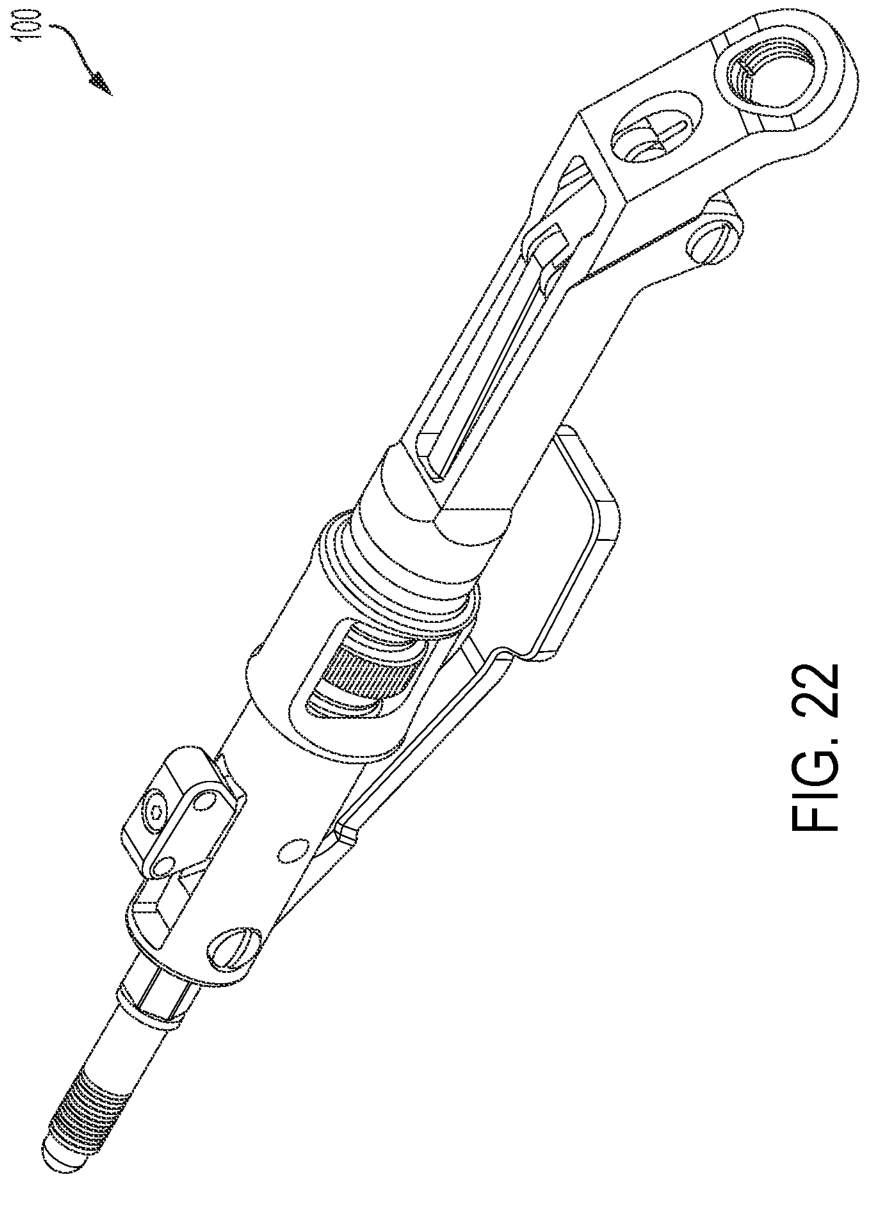
FIGS. 22-28 are various views of an implant extractor design in accordance with the subject disclosure.
Figure 23:
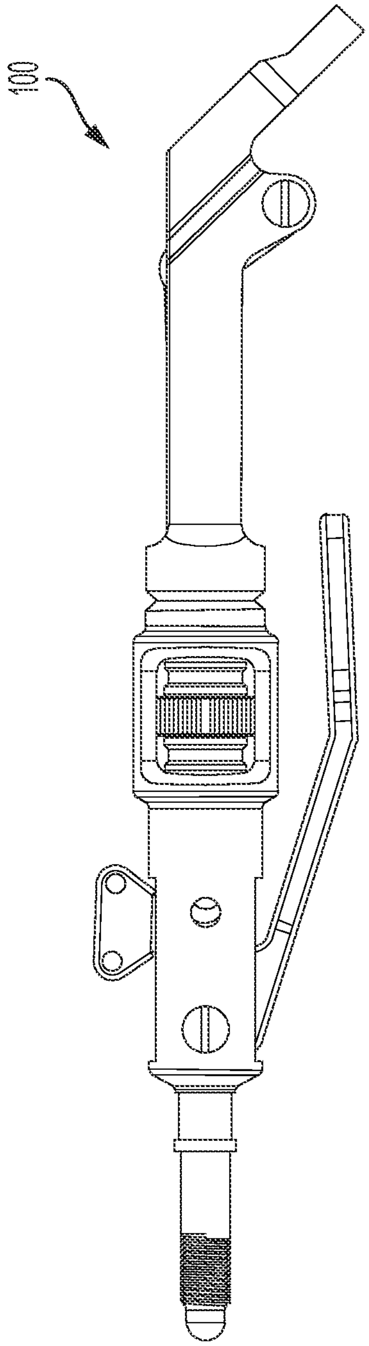
Figure 24:
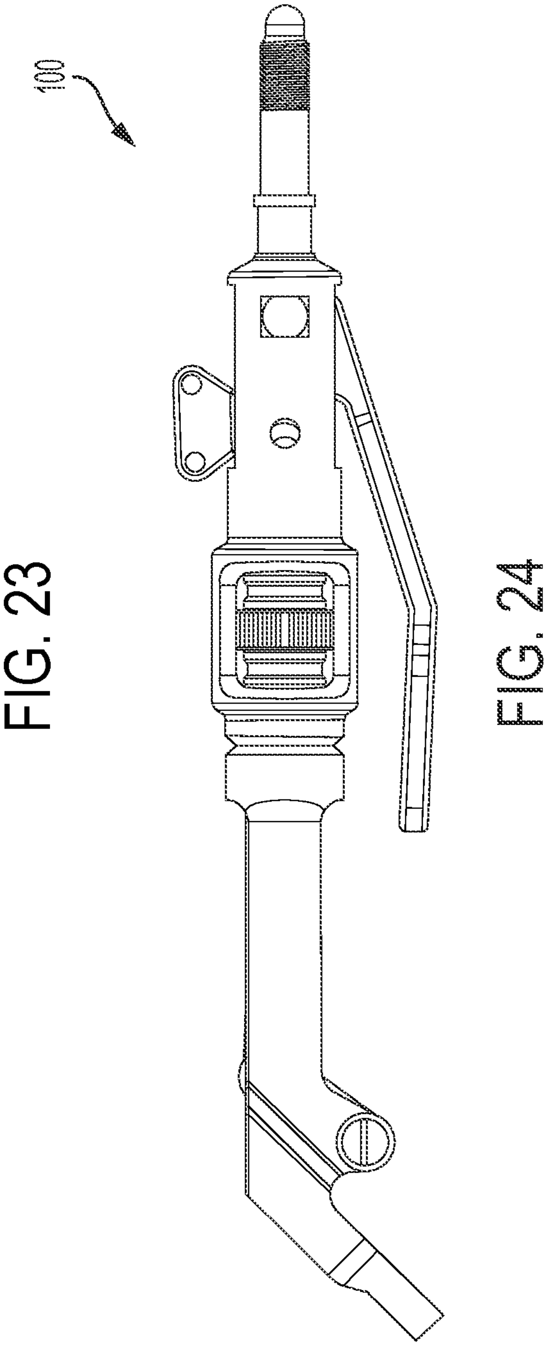
Figure 25:
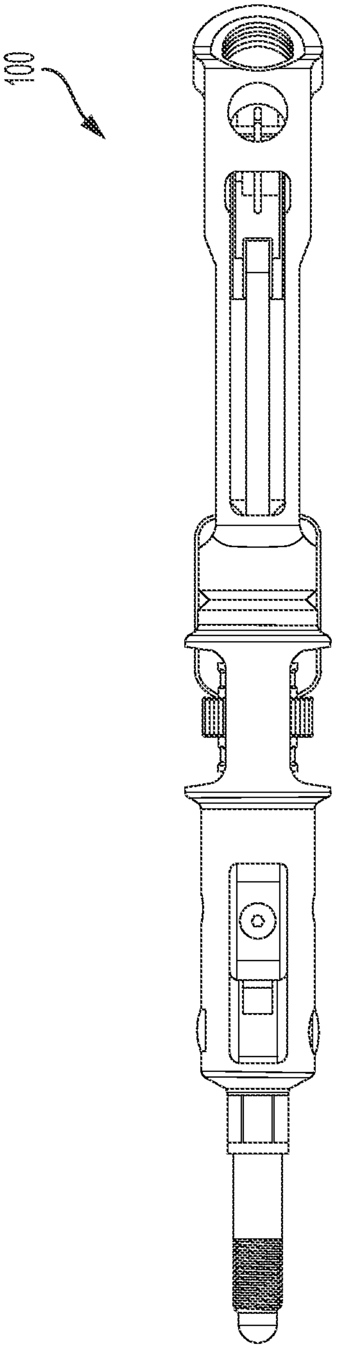
Figure 26:
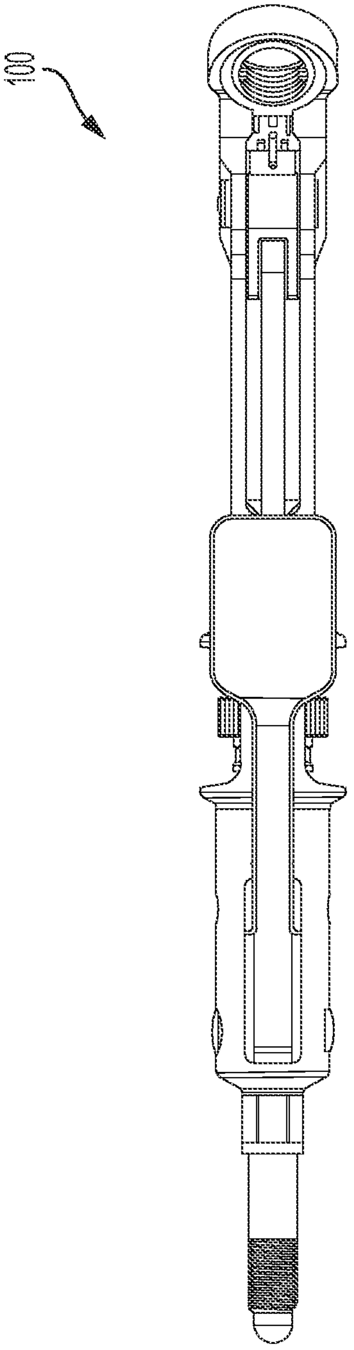
Figure 28:
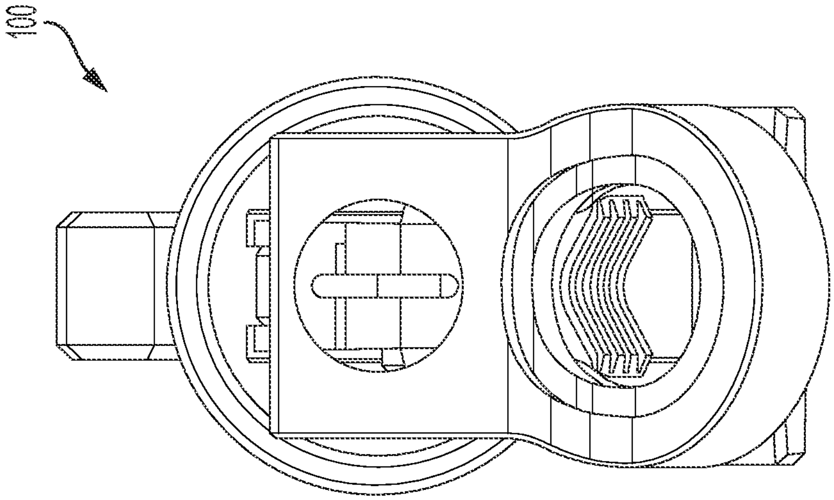
Figure 27:
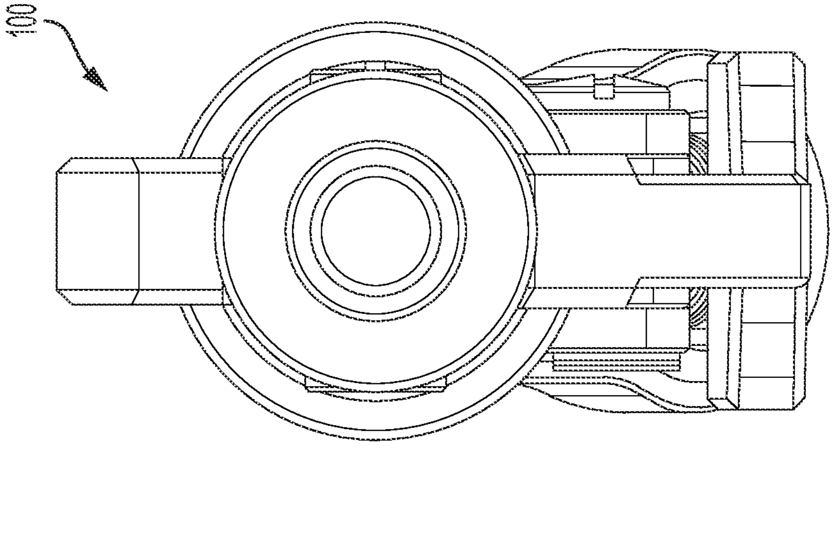

According to an aspect, and as best shown in FIGS. 1, 18 & 21, the hip stem implant extractor 100 further comprises a locking key 140 connected to the proximal link 112 by a fastener 146 and rotatable about the fastener 146 in the direction of arrows B (FIG. 21) relative thereto between the unlocked position 170 (FIG. 17) and a locked position 172 (FIG. 18) extending substantially 90 degrees with respect to the unlocked position. As shown in FIGS. 19 & 20, the proximal link 112 may also include two sockets 150 within which are disposed springs 148 the upper ends of which biasingly support ball bearings 152. The spring-loaded ball bearings mate with two pairs of detents 151 to ensure that the locking key does not turn during extraction impacts. The mating ball bearings and detents also provide positive tactile feedback that the locking key 140 is firmly in its locked or unlocked position. In the unlocked position of the locking key, the handle 106 is free to move between its unlocked and locked positions. In the locked position of the locking key, the handle 106 is locked into its locked position whereby the jaw 118 is locked in its grip engaging position e.g., in gripping engagement with a hip stem implant trunnion, and extracting forces such as impacts may be applied to an extraction tool attached to the threaded connector 104 of the proximal body member 102.

The locking key 140 is operatively connected to the proximal link 112 and moveable between an unlocked position and a locked position. The locking key 140 locks the position of the proximal link 112 in a fixed position.

Having described the orientation and assembly of the various components of the hip stem implant extractor 100, its features become apparent. For example, the various links making up the linkage assembly 280 can be optimized to provide optimal clamping force by the jaw while minimizing the overall longitudinal length of the housing 100, thereby allowing a short hip stem implant extractor 100 e.g., a hip stem implant extractor that is shorter compared to conventional hip stem implant extractors.

Moreover, the linkage assembly's pivotal engagement of the jaw holds the jaw in a commanded position even if there is no force beyond gravity acting on the jaw. In contrast, gravity acting on conventional sliding trunnion engaging structures can freely slide the engaging structure into undesirable positions when a commanding force of the device is removed, or the device is in a non-locking state. Also, since the sliding jaw and the insert of the linkage assembly are detachably secured to the housing, they can be easily removed and replaced as needed in case these structures wear, without requiring the replacement of expensive surrounding components.

In other words, the hip stem implant extractor 100 provides a first engaging force or fine engaging force via the linkage assembly to position the jaw in the commanded position. The hip stem extractor also provides a second engaging force or locking force via the cam lock for securely engaging the jaw to the implant to be extracted.

In accordance with another aspect of the subject disclosure, FIGS. 22-28 illustrate a design of the implant extractor. The relatively light intermittently broken surface shading depicts contour, not surface decoration. The broken surface shading lines shown throughout the figures depicts contours of the surgical tool. Various portions of the implant extractor design can be illustrated in broken lines to depict portions that form no part of the design.

While the subject disclosure has been described with reference to exemplary embodiments, it will be appreciated by those skilled in the art that various changes may be made, and equivalents may be substituted for elements thereof without departing from the scope of the subject disclosure. In addition, modifications may be made to adapt a particular situation or material to the teachings of the exemplary embodiments without departing from the essential scope thereof. It is to be understood, therefore, that the exemplary embodiments are not limited to the particular aspects disclosed, but it is intended to cover modifications within the spirit and scope of the subject disclosure as defined by the appended claims.

The invention claimed is:

1. An implant extractor for operably engaging a surgical implant, the implant extractor comprising:

a housing having a proximal end configured for connection to an extraction tool, a distal end for operably engaging an implant, and a jaw at the distal end of the housing; and a linkage assembly mounted within the housing, the linkage assembly including a linkage pivotally secured to the jaw such that operation of the linkage assembly moves the jaw towards and away from the distal end, wherein the linkage assembly includes:

a rod assembly, a proximal link operatively connected to the rod assembly and wherein a proximal end of the rod assembly is pivotably connected to a distal end of the proximal link, an intermediate link operatively connected to the rod assembly, and a bell link operatively connected to the intermediate link and the jaw.

2. The implant extractor of claim 1, wherein the housing includes a distal body member having an opening for receiving the implant.

3. The implant extractor of claim 1, wherein the housing further includes an elongate recess and a distal body member having an opening in fluid communication with the elongate recess.

4. The implant extractor of claim 1, further comprising a handle pivotably connected to the housing and operatively engaged with the linkage assembly.

5. The implant extractor of claim 1, wherein the jaw is detachably secured within the housing.

6. The implant extractor of claim 1, further comprising a removable insert detachably secured to the housing about its distal end, the removable insert having a surface for engaging the implant and an opening for receiving the jaw therethrough.

7. The implant extractor of claim 1, further comprising a cam lock configured to lock the linkage assembly in a fixed position.

8. The implant extractor of claim 1, further comprising a cam lock configured to apply a locking force and lock the linkage assembly in a fixed position.

9. The implant extractor of claim 1, further comprising a handle pivotably connected to the housing and operatively engaged with the rod assembly.

10. The implant extractor of claim 9, wherein the handle is movable between a first position causing the jaw to move to a disengagement state, and a second position causing the jaw to move to an engagement state.

11. The implant extractor of claim 1, wherein the rod assembly is a telescopic rod assembly.

12. The implant extractor of claim 1, wherein the rod assembly comprises:

a proximal link connector operatively connected to the proximal link;

an intermediate link connector operatively connected to the intermediate link; and a rotatable shaft rotatable about the proximal link connector and operatively engaged with the intermediate link connector.

13. The implant extractor of claim 12, further comprising a dial operatively connected to the central rotatable shaft, whereby rotation of the dial in a first direction operates to unthread the intermediate link connector from the central rotatable shaft, and whereby rotation of the dial in a second direction opposite the first direction operates to thread the intermediate link connector into the central rotatable shaft.

14. The implant extractor of claim 1, further comprising a jaw link coupling the bell link to the jaw.

15. The implant extractor of claim 1, further comprising a locking key operatively connected to the proximal link and moveable between an unlocked position and a locked position.

16. The implant extractor of claim 15, wherein the locking key locks the position of the proximal link in a fixed position.

17. An implant extractor comprising:

a housing that includes:

a recess extending therein, a proximal end for connecting to an extraction tool, a distal end for operatively engaging a surgical implant, a distal body member having an opening for receiving an implant, and a jaw at the distal end of the housing and operatively mounted to the distal body member;

a linkage assembly mounted within the recess, the linkage assembly including:

a rod assembly, a proximal link operatively connected to the rod assembly, wherein a proximal end of the rod assembly is pivotably connected to a distal end of the proximal link, an intermediate link operatively connected to the rod assembly, and a bell link operatively connected to the intermediate link and the jaw;

a handle pivotably connected to the housing and operatively engaged with the linkage assembly to move the jaw between an engaged position and a disengaged position; and a cam lock for locking the linkage assembly in a fixed position.

* * * * *